United States Patent [19]
Budding

[11] Patent Number: 5,464,412
[45] Date of Patent: Nov. 7, 1995

[54] SOLO OPERATED HEMORRHOID LIGATOR RECTOSCOPE

[76] Inventor: Jacobus Budding, 20 Lessies Dr., Poquoson, Va. 23662

[21] Appl. No.: 273,863

[22] Filed: Jul. 12, 1994

[51] Int. Cl.⁶ ..................................... A61B 17/00
[52] U.S. Cl. ........................... 606/140; 606/139
[58] Field of Search ..................... 606/140, 141, 606/139, 135, 165

Primary Examiner—Tamara L. Graysay
Assistant Examiner—Jeffrey A. Schmidt

[57] ABSTRACT

A surgical instrument for elastic ring ligation of hemorrhoids and other anatomical features, by a solo-operator. The essence of the device is a double barreled endoscope comprising of an exterior barrel (4) and a closely fitting interior barrel (6) receivable within the exterior barrel. The construction of the endoscope enables the operator to insert the tool into a body orifice, single handedly, with the right or the left hand without adjustment of the instrument. The distal end of the interior barrel is loaded with a contractible elastic ring (10) aided by a loading mandrel (14). The instrument is placed inside the orifice, the obturator removed and accurate positioning brings the target area into view. The selected tissue is drawn into the interior barrel which functions as ligator. The operator can pull the flange like trigger of proximal end of the interior barrel which retracts the barrel, causing the elastic band to be released by the exterior barrel. The tool is easy to clean and sterilize. The device is much simpler and a larger amount of tissue can be captured within the elastic band than with prior art.

2 Claims, 1 Drawing Sheet

2. HANDLE.
4. EXTERIOR BARREL.
6. INTERIOR BARREL.
8. FLANGE LIKE TRIGGER.
10. CONTRACTIBLE ELASTIC BAND. (POSITIONS OVER TIP OF PART 6.)
12. OBTURATOR.
14. ELASTIC BAND LOADING MANDREL.

SOLO OPERATED HEMORRHOID LIGATOR RECTOSCOPE.

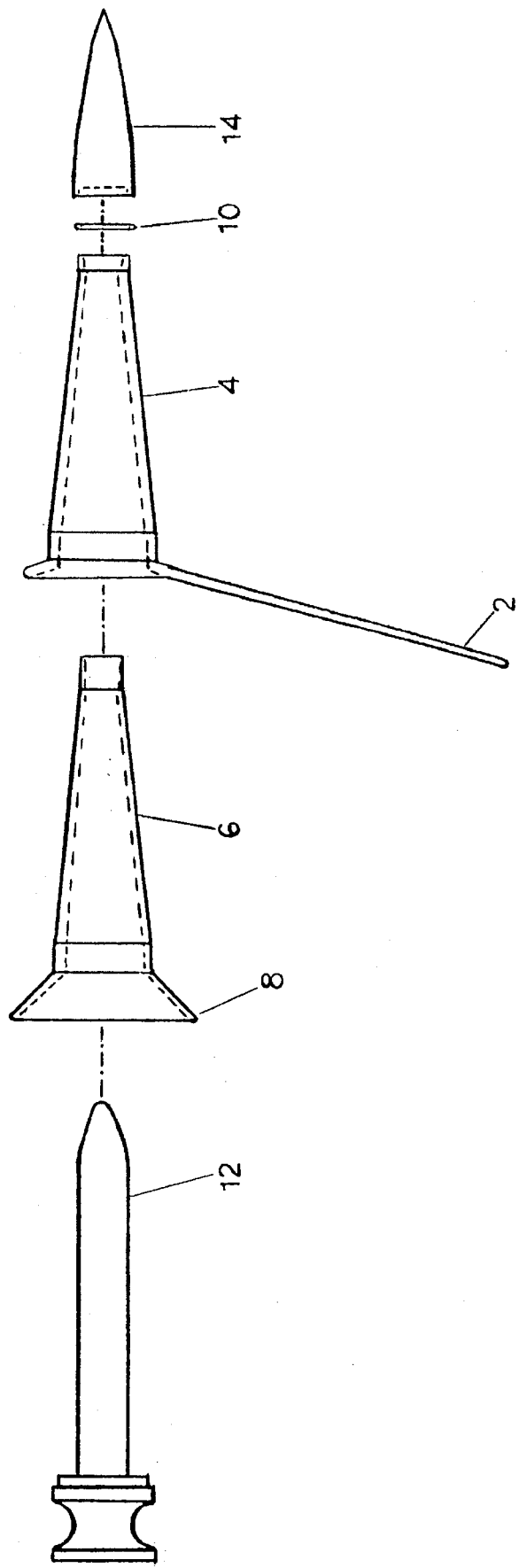
2. HANDLE.
4. EXTERIOR BARREL.
6. INTERIOR BARREL.
8. FLANGE LIKE TRIGGER.
10. CONTRACTIBLE ELASTIC BAND. (POSITIONS OVER TIP OF PART 6.)
12. OBTURATOR.
14. ELASTIC BAND LOADING MANDREL.
SOLO OPERATED HEMORRHOID LIGATOR RECTOSCOPE.

SOLO OPERATED HEMORRHOID LIGATOR RECTOSCOPE

BACKGROUND—FIELD OF INVENTION

The invention relates to an improved, simplified, surgical tissue ligating tool specifically to a solo-operator device for treating hemorrhoids.

BACKGROUND—DESCRIPTION OF PRIOR ART

Internal hemorrhoids and anal mucosal prolapse are the cause for morbidity of many people all over the world. The banding technique, using the elastic ring ligator, has become the treatment of choice for internal hemorrhoids. Most prior art ligators require a team of a surgeon and an assistant to complete the procedure.

Conventionally the surgeon introduces the endoscope inside the patient and brings an anatomical feature into view. At this point he hands control of the tool to an assistant. This frees his own hands to pick up a ligator and a tissue grasping tenaculum. The ligator and tenaculum are both introduced and precisely positioned inside the endoscope. To complete the elastic band ligating procedure the operator pulls the selected tissue inside the ligator ring and then releases the contractible elastic band around the hemorrhoid. This causes the strangulated tissue to necrose and seven to ten days later the necrosed tissue separates from the body. This tissue is ultimately eliminated in a natural way.

The different tools inside the endoscope tend to obstruct the view of the operator. The assistant cannot see inside the instrument, and loss of the target area or loss of line of sight of the operator frequently occurs because small motions of the assistant' hand can change the position of the tool.

Prior art has attempted to craft a tool that would allow a solo-operator procedure but problems have remained. Although freeing up one hand, other difficulties were created. The tool and the procedure became more complex. Some tools and parts are hard to clean and require additional pieces of equipment such as vacuum suction (U.S. Pat No. 5,203,863 to Bidoia, Apr. 20, 1993). Other devices suffer from visual obstruction and are not user friendly (U.S. Pat. No. 5,158,563 to Cosman Oct. 27, 1992).

A combined endoscope-ligator was developed by Van Hoom (U.S. Pat. No. 3,760,810 to Van Hoorn, Sep. 25, 1973). The instrument is very complicated with many parts, which makes it virtually impossible to mechanically clean and sterilize. It is difficult to operate.

The simplifications, the double barrel construction of the endoscope and the exposed distal portion of the interior barrel serving as ligator in the instrument of my invention, is a novel presentation.

OBJECTS AND ADVANTAGES

Accordingly, several objects and advantages of my invention are, that the operator can complete the entire ligating procedure single handedly. The tool is simple, easy to use and clean. The surgeon is already familiar with the anoscope and no new techniques have to be learned. No special adjustments of the tool are necessary whether the operator is left or right handed. The light source is external and can be either a ceiling mounted light fixture or a portable headlight. Both are universally available to those in the profession in a position to do these procedures. There are no batteries necessary internal lighting. In a permanent version of the instrument of the invention, the components have simple lines and are easy to clean and re-sterilize. There are no complicated mechanical, moving parts or springs and no small openings that can clog up with debris. The operator can use his own favorite tissue grasping tenaculum whether using a permanent or a disposable version of time instrument. The operator maintains full control over the smallest details of the procedure. This is very important since it is a very delicate operation. Precise positioning of the endoscope is mandatory and can mean the difference between success or failure of the operation. Using the instrument of the invention during the banding procedure, the operator can constantly make minute changes in position and alignment. He can keep the target area in focus and hold it in the proper position for grasping and pulling the anatomical feature inside the ligator portion of the device. In order to make these frequent fine adjustments, adequate eye to hand coordination is essential, which is lost when the operator has to rely an assistant for holding the endoscope. The tool will be available in several sizes. The medium and large sizes will have a greater internal diameter of the ligator portion of the interior barrel, than prior art tools.

This enables the operator to pull inside the barrel and ligate, a larger amount of tissue than possible with prior art ligating instruments.

DRAWING FIGURES

Drawing no. 1 is the only drawing and shows the endoscope, obturator, elastic band and loading mandrel.

Reference Numerals In Drawing
2. handle
4. exterior barrel
6. interior barrel
8. flange like trigger
10. contractible elastic band
12. obturator
14. elastic band loading mandrel

DESCRIPTION FIGURE 1

A typical embodiment of the present invention is illustrated in FIG. 1. The elements of the endoscope are exterior barrel 4, interior barrel 6, handle 2, trigger 8, contractible elastic band 10, obturator 12 and elastic band loading mandrel 14. The endoscope functions simultaneously as rectoscope and elastic band ligator. The obturator fits inside the interior barrel and emerges from the distal end of said interior barrel when inserted into said barrel. The obturator is attached to a shaft and a handle for insertion and extraction. The loading mandrel slips over and around the distal end of the interior barrel making loading more secure.

From the description above, a number of advantages of my tool become evident:

(a) The tool is much simplified with fewer parts than prior art.

(b) It is simple to operate.

(c) It is easy to care for.

(d) There are no small holes or crevices.

(e) There are no small delicate parts.

(f) There are no springs or levers.

(g) Either operator hand can hold and manipulate the handle and pull the trigger at an opportune time.

(h) The tool does not require special adjustment for right or left handed operators.

(i) The view is uncluttered by other tools such as a ligator or other paraphernalia.

(j) The flange like trigger is an integral part of the proximal end of the internal barrel.

Operation-FIG. 1

The instrument according to the invention can be prepared for operation as follows. First, interior barrel 6 is inserted and fully advanced into exterior barrel 4. This exposes the distal end of the interior barrel. Elastic band 10 is loaded onto mandrel 14. The mandrel is placed on and over the distal end of the interior barrel. The elastic band is pushed manually from the mandrel onto said distal end of the interior barrel. The mandrel is removed and put aside. With the contractible elastic band in place, obturator 12 is fully inserted into the interior barrel. This provides a smooth transition from obturator, to interior barrel, to elastic band and to exterior barrel. The tool is now ready for the planned surgical procedure.

The procedure for contractible elastic ring ligation of hemorrhoids using the instrument according to the invention is as follows: A copious amount of lubricant is applied to the distal end of the rectoscope. The instrument of the invention is introduced with one hand into the patient' anus. Obturator 12 is removed, opening interior barrel 6 which now can function as a rectoscope. Illuminated by an external light source, under direct view, the tool is manipulated by small too and fro motions or angulation. This brings the target area in a position so that the anatomical structure can be identified and grasped with a tenaculum, held in the other hand. A tier selection of the hemorrhoid the surgeon pulls the tissues inside the distal end of interior barrel 6. Trigger 8 at the proximal end of said interior barrel is pulled with the hand holding the handle causing a longitudinal sliding retraction of said interior barrel. The distal end of exterior barrel 4 opposes the retraction of contractible elastic band 10 and pushes it off the distal end of interior barrel 6. The band contracts around the base of the retracted hemorrhoid. The grasping tenaculum is removed first and then the endoscope. The same tool can be reloaded for an additional procedure on the same patient when indicated.

SUMMARY, RAMIFICATIONS AND SCOPE

Accordingly the reader will see that the instrument of the invention comprises a double barreled endoscope that functionally combines a rectoscope and a hemorrhoid ligator into one tool. The operator can insert the tool of the invention with one hand, remove the obturator with the other hand and make the necessary adjustments in position of the tool for viewing the anatomical features. When the surgeon is ready to release the contractible elastic band around a selected anatomical feature, he pulls the trigger with a finger on the hand that holds the handle of the endoscope and complete the procedure by removing the grasping tenaculum and the rectoscope. The solo application of this banding procedure has great advantages for the patient and the surgeon. It offers a less complicated procedure with simplified equipment, greater accuracy and greater effectiveness. When needed, an instrument with greater inside diameter of the distal end of the interior barrel can be selected. A contractible elastic band can be placed around a larger amount of tissue than possible with prior art tools.

It will be apparent that the instrument of the invention can be useful for elastic ring ligation of hemorrhoids, but can be used for elastic ring ligation of other anatomical structures or lesions located within various orifices, whether in humans or in animals. In the construction and manufacture of the instrument of the invention various designs, sizes, materials and thickness of the materials are anticipated.

Although the description above contains many specificities, these should not be construed as limiting the scope of the invention but merely as providing illustrations of some of the presently preferred embodiments of this invention.

Thus the scope of the invention should be determined by the appended claims and their legal equivalents, rather than by the examples given.

I claim:

1. A double barreled endoscopic probe, having a longitudinal axis, comprising a conical exterior barrel, having a wall inclined with respect to the longitudinal axis and a conical interior barrel having a wall inclined with respect to the longitudinal axis and parallel to the wall of the exterior barrel, the interior barrel is longer than the than the exterior barrel, the distal end of the interior barrel provides a means for holding a contractile elastic ring in stretched condition, the proximal end of the interior barrel includes a flange which acts as a trigger means to actuate retraction of the interior barrel with respect to the exterior barrel whereby the elastic ring is pushed from the interior barrel, the proximal end of the the exterior barrel includes a handle for manipulation of the probe.

2. The double barreled endoscopic probe of claim 1, further comprising an obturator to facilitate insertion and a mandril to facilitate loading the tool with the contractile elastic ring, short cylindrical sections at the proximal and distal ends of the interior and exterior barrels, providing smooth parallel motion of the barrels relative to each other.

* * * * *